United States Patent [19]

Bianconi et al.

[11] Patent Number: 5,026,884
[45] Date of Patent: Jun. 25, 1991

[54] REDUCTIVE COUPLING OF CARBON COMPOUNDS VIA TRANSITION METAL COMPLEXES

[75] Inventors: Patricia A. Bianconi, Boalsburg, Pa.; Stephen J. Lippard, Cambridge, Mass.; Chebrolu P. Rao, Bombay, India; Raymond N. Vrtis, Cambridge, Mass.

[73] Assignee: Massachusetts Institute of Technology, Cambridge, Mass.

[21] Appl. No.: 311,931

[22] Filed: Feb. 16, 1989

Related U.S. Application Data

[63] Continuation-in-part of Ser. No. 78,305, Jul. 27, 1987, abandoned, which is a continuation-in-part of Ser. No. 761,399, Aug. 1, 1985, Pat. No. 4,683,315.

[51] Int. Cl.$^5$ ................................................. C07F 7/02
[52] U.S. Cl. ........................................ 556/12; 556/9; 556/43
[58] Field of Search ................................ 556/9, 12, 43

[56] References Cited

U.S. PATENT DOCUMENTS 4,683,315  7/1987  Lippard et al. ........................ 556/12

OTHER PUBLICATIONS

Liebig, J. Ann. Chem. Pharm., 11, 182 (1834).
Joannis, Hebd. Seances. A.C.R. Acad. Sci., 116, 1518 (1893), ibid., 158, 874 (1914).
Pearson, Nature, vol. 131, p. 166 (1933).
Hackspill et al., Hebd. Seances. A.C.R. Acad. Sci., 206, 1818 (1938).
Scott, Science, vol. 115, p. 118 (1952).
Weiss, et al., Helv. Chim. Acta, 46, 1121 (1963); ibid., 47, 1415 (1964).
Buchner, Helv. Chim. Acta., 46, 2111 (1963).
Weiss et al., Chem. Ber., 98, 126 (1965).
Weiss et al., Z. Anorg. Allgem. Chem., 330, 251 (1964).
Ellis et al., J. Am. Chem. Soc., vol. 103, p. 6100 (1981).
Silvestri et al., Gazz. Chim. Ital., vol. 102, p. 818 (1972).
Silvestri et al., Electrochim. Acta, vol. 23, p. 413 (1978).
Bockmair et al., Z. Naturforsch. B., Anorg. Chem., Org. Chem., 30B, 330 (1975).
Uribe et al., J. Electroanal. Chem., vol. 152, p. 173 (1983).
Buchner, Helv. Chim. Acta, 48, 1229 (1965).
Manriquez, et al., J. Am. Chem. Soc., vol. 100, p. 2716 (1978).
Wolczanski et al., Acc. Chem. Res., vol. 13, p. 121 (1980).
Berry et al., J. Am. Chem. Soc., vol. 104, p. 4712 (1982).
Fagan et al., J. Am. Chem. Soc., vol. 103, p. 6959 (1981).
Katahira et al., Organometallics, vol. 1, p. 1723 (1982).
Gambarotta et al., J. Am. Chem. Soc., vol. 105, p. 7295 (1983).
Evans et al., J. Chem. Soc., Chem. Commun., p. 706 (1981).
Evans et al., J. Am. Chem. Soc., vol. 107, p. 3728 (1985).
Planalp et al., J. Am. Chem. Soc., vol. 105, p. 7774 (1983).

(List continued on next page.)

*Primary Examiner*—Patrick P. Garvin
*Assistant Examiner*—George Fowson
*Attorney, Agent, or Firm*—Ernest V. Linek; George W. Neuner

[57] ABSTRACT

The present invention is directed to a process for the formation of an isolable $C_2$ containing compound formed by reductive coupling chemistry, and specifically to a superior synthetic method for the reactions:

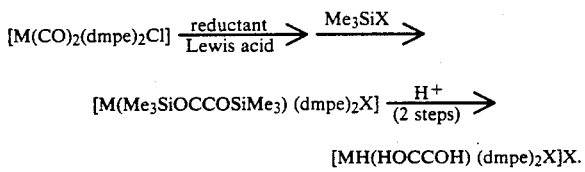

19 Claims, 4 Drawing Sheets

OTHER PUBLICATIONS

Erker et al., Angew, Chem. Int. Ed. Engl., vol. 25, p. 364 (1986).
Arnold et al., J. Am. Chem. Soc., vol. 107, p. 6409 (1985).
Lam et al., J. Am. Chem. Soc., vol. 99, p. 617 (1977).
Corfield et al., Inorg. Chem., vol. 20, p. 922 (1981).
Dewan et al., Inorg. Chem., vol. 20, p. 4069 (1981).
Giandomenico et al., Inorg. Chem., vol. 104, p. 1263 (1982).
Carvana et al., Inorg. Chem., vol. 21, p. 1860 (1982).
Hoffman et al., J. Am. Chem. Soc., vol. 105, p. 146 (1983).
Warner et al., Organometallics, vol. 5, p. 1716 (1986).
Cotton et al., J. Am. Chem. Soc., vol. 105, p. 3734 (1983).
Cotton et al., J. Am. Chem. Soc., vol. 106, p. 6987 (1984).
Lenz et al., Angew. Chem. Int. Ed. Engl., vol. 23, p. 525 (1984).
Hoffman et al., J. Am. Chem. Soc., vol. 105, p. 146 (1983).
Datta et al., Inorg. Chem., vol. 16, p. 1134 (1977).

REDUCTIVE COUPLING OF CARBON COMPOUNDS VIA TRANSITION METAL COMPLEXES

STATEMENT OF GOVERNMENT INTEREST

The Government of the United States has certain rights in this invention pursuant to Grant No. CHE 85-42205 awarded by the National Science Foundation.

CROSS-REFERENCE TO RELATED APPLICATION

The present invention is a continuation-in-part of copending application Ser. No. 07/078,305, filed 27 July 1987, now abandoned, which is a continuation-in-part of application Ser. No. 761,399, filed 8/1/85, now U.S. Pat. No. 4,683,315, the disclosures of both of which, to the extent necessary, are hereby incorporated herein by reference.

BACKGROUND OF THE INVENTION

The formation of carbon-carbon bonds has long been a challenge to synthetic chemists. One such C—C bond-making process that is both intellectually appealing and of potential practical value is to convert carbon monoxide into functionalized hydrocarbons by reaction chemistry in which the first step involves reductive coupling. One reductive coupling example is the direct reduction of CO by alkali metals (see, Liebig, *J. Ann. Chem. Pharm.*, 11, 182 (1834); Joannis, *Hebd. Seances. A.C.R. Acad. Sci.*, 116, 1518 (1893); ibid., 158, 874 (1914); Pearson, *Nature*, 131, 166 (1933); Hackspill et al., *Hebd. Seances. A.C.R. Acad. Sci.*, 206, 1818 (1938); Scott, *Science*, 115, 118 (1952); Weiss, et al., *Helv. Chim. Acta.*, 46, 1121, (1963); *Ibid.*, 47, 1415 (1964); Büchner, *Helv. Chim. Acta*, 46, 2111 (1963); Weiss, et al., *Z. Anorg. Allgem. Chem.*, 330, 251 (1964); Weiss, et al., *Chem. Ber.*, 98, 126 (1965); and Ellis, et al., *J. Am. Chem. Soc.*, 103, 6100 (1981)).

Another such method is electrochmical reductive coupling (see, Silvestri, et al., *Gazz. Chim. Ital.*, 102, 818 (1972); Silvestri, et al, *Electrochim. Acta*, 23, 413 (1978); Bockmair, et al., *Z. Naturforsch. B.: Anorg. Chem., Org. Chem.*, 30B, 330 (1975); and Uribe, et al., *J. Electroanal. Chem.*, 152, 173 (1983)).

These two techniques both yield the species $M_2(C_2O_2)$ and higher oligomers, from which, upon further redox or solvolysis reactions, glycolic acid derivatives, ethylene glycol, oxalic acid, hexahydroxybenzene, and aci-reductone polymers have been isolated. See, in addition, to the previous citatons, Büchner, *Helv, Chim. Acta*, 48, 1229 (1965); and Barber, Ph.D. Thesis, Chapter III, Massachusetts Institute of Technology, 1981.

Reductive coupling of carbonyl ligands in soluble transition, lanthanide, or actinide metal complexes has also been achieved. (See, for example, Manriquez, et al., *J. Am. Chem. Soc.*, 100, 2716 (1978); Wolczanski, et al., *Acc. Chem. Res.*, 13, 121 (1980); Barry, et al., *J. Am. Chem. Soc.*, 104, 4712 (1982); Fagan, et al., *J. Am. Chem. Soc.*, 103, 6959 (1981); Katahira, et al., *Organometallics*, 1, 1723 (1982); Gambarotta, et al., *J. Am. Chem. Soc.*, 105, 7295 (1983); Evans, et al., *J. Chem. Soc., Chem. Commun.*, 706 (1981); Evans, et al., *J. Am. Chem. Soc.*, 107, 3728 (1985); Planalp, et al., *J. Am. Chem. Soc.*, 105, 7774 (1983); Erker, et al., *Angew. Chem. Int. Ed. Engl.*, 25, 364 (1986); and Arnold, et al., *J. Am. Chem. Soc.*, 107, 6409 (1985)).

This approach affords better control of subsequent reaction products and stereochemistry. In the cases reported thus far, however, the oxygen atoms of the coupled ligand are coordinated to a metal atom.

In recent years Lippard and his coworkers have been investigating the reductive coupling of alkyl isocyanide ligands in seven-coordinate complexes of the form $[M(CNR)_6X]^+$ (M=Mo and W; X=halide or cyanide). (See also, Lam, et al., *J. Am. Chem. Soc.*, 99, 617 (1977); Corfield, et al., *Inorg. Chem.*, 20, 922 (1981); Dewan, et al., *Inorg. Chem.*, 20, 4069 (1981); Giandomenico, et al., *J. Am. Chem. Soc.*, 104, 1263 (1982); Caravana, et al., *Inorg. Chem.*, 21, 1860 (1982); and Hoffmann et al., *J. Am. Chem. Soc.*, 105, 146 (1983)). Also under investigation have been complexes of the form $[Mo(CNR)_4(bpy)Cl]^+$. (See, Warner et al., *Organometallics*, 5, 1716 (1986)).

These two complexes may be illustrated by the following two equations:

(eq. 1)

(eq. 2)

Similar coupling reactions occur for Nb, Ta, and Mo complexes where, in the products, the coupled isocyanide ligand, formally the $RNCCNR^{2-}$ dianion, bridges two metal centers. (See, for example, Cotton, et al., *J. Am. Chem. Soc.*, 105, 3734 (1983); Cotton, et al., *J. Am. Chem. Soc.*, 106, 6987 (1984); and Lenz, et al., *Angew. Chem. Int. Ed. Engl.*, 23, 525 (1984)).

From these experimental studies and extended Hückel molecular orbital calculations (Hoffmann et al., *J. Am. Chem. Soc.*, 105, 146 (1983)) Lippard and his coworkers have identified several factors that promote the isocyanide reductive coupling reaction. Specifically, it has been discovered that eqs. (1) and (2) are favored by the high coordination numbers of the transition metals, the use of linear or chelating ligands, proper orbital alignment during the coupling step, an electron rich metal center and the need for a Lewis acid to bind the heteroatoms of the coupled ligand.

Using these factors as a guideline, Lippard and his coworkers searched for, and have now identified, a system in which reductive coupling of two carbon containing ligands, e.g., the carbon monoxide ligands in the known seven-coordinate $[M(CO)_2(dmpe)_2Cl]$ complexes, [M=Nb, Ta and dmpe=1,2-bis(dimethylphosphino)ethane] (see, Datta, et al., *Inorg. Chem.*, 16, 1134 (1977)) can be readily achieved.

SUMMARY OF THE INVENTION

The present invention is directed to a process for the formation of an isolable $C_2$ containing compound formed by reductive coupling chemistry, and preferably to a superior synthetic method for the reaction of equation (3):

(eq. 3)

-continued

[M(Me₃SiOCCOSiMe₃)(dmpe)₂Y]

Two related synthetic routes to the reductively coupled products of equation 3 make up the present invention.

As shown in eq. 3, a reducing agent is first added to a solution containing the starting material. In one route (Method B), the reducing agent (reductant) is magnesium dust, activated by for example, $I_2$, $HgCl_2$, and the like, which is followed by addition of a Group IV metallocene dihalide (e.g., $(C_5Me_5)_2ZrCl_2$) as a Lewis acid. In the more preferred second route (Method A), 40% sodium amalgam was used as both reductant and Lewis acid, the latter presumably being solvated $Na^+$ ions.

The 40% sodium amalgam (Na/Hg) reductive coupling procedure of the present invention (Method A) is especially preferred over the activated Mg route (Method B) as it requires less expensive starting materials and simpler reaction conditions.

Also disclosed are the crystal structures of four reductively coupled products, Compound (1), M=Nb, Y=Cl; Compound (2), M=Ta, Y=Cl; Compound (3), M=Ta, Y=0.8 Cl and 0.2 I; and Compound (4), M=Ta, Y=OTf (OTf=$O_3SCF_3$).

The reductive coupling of two carbon monoxide ligands to form coordinated alkynes has been found to occur in good yield for the seven-coordinate starting materials, Compound (5), [Nb(CO)₂(dmpe)₂Cl] and Compound (6), [Ta(CO)₂(dmpe)₂Cl]. The resulting coupled species, herein designated Compounds (1), (2), (3), and (4), have the following formulae:

[Nb(Me₃SiOCCOSiMe₃)(dmpe)₂Cl]

[Ta(Me₃SiOCCOSiMe₃)(dmpe)₂Cl]

[Ta(Me₃SiOCCOSiMe₃)(dmpe)₂Cl₀.₈I₀.₂]

and

[Ta(Me₃SiOCCOSiMe₃)(dmpe)₂(OTf)]

In another embodiment of the present invention, the reaction of compound (2), [Ta(Me₃SiCCOSiMe₃)(dmpe)₂Cl], with aqueous HCl affords [TaH(HOCCOH)(dmpe)₂Cl]Cl (7). The geometry at the tantalum center in compound (7) is best described as a pentagonal-bipyramid with the four atoms of two dmpe ligands and the hydride atom defining the pentagonal plane, and axial positions occupied by the chloride ligand and the midpoint of the HO-C≡C-OH triple bond. This is the first known molecule containing the dihydroxyacetylene ligand.

Formation of (7) from (2) occurs formally in two steps, protiolysis to form the dihydroxyacetylene ligand and oxidative addition of $H^+$ to the tantalum center to form a tantalum hydride bond.

BRIEF DESCRIPTION OF THE DRAWINGS

[M(R₃SiOCCOSiR₃)(dmpe)₂Y]

where dmpe=bis(1,2-dimethylphosphino)ethane, R is $C_1$ to $C_6$ alkyl, preferably $CH_3$, M is Ta or Nb, and Y is halogen, preferably Cl or I. In Compound (1), M=Nb, Y=Cl; Compound (2), M=Ta, Y=Cl; and Compound (3), M=Ta, Y=Cl₀.₈I₀.₂.

DETAILED DESCRIPTION OF THE PREFERRED EMBODIMENTS

Reductive coupling of two carbon monoxide ligands occurs when seven-coordinated niobium(I) and tantalum(I) complexes are reduced in the presence of a Lewis acid and subsequently treated with trimethylsilyl chloride or triflate (eq. 3).

The [M(CO)₂(dmpe)₂Cl] complexes were identified as good candidates for promoting this reaction for several reasons. X-ray structural studies revealed close non-bonded contacts between the two carbonyl carbon atoms, situated on the unique edge of $C_{2v}$ capped trigonal prisms, for [Nb(CO)₂(dmpe)₂Cl], 2.30, 2.29 Å; [Nb(CO)₂(dmpe)₂I], 2.24(12) Å; and [Ta(CO)₂(dmpe)₂Me], 2.29 Å, and C-M-C angles of 70° or less. (See, Bianconi, Ph.D Thesis, Massachusetts Institute of Technology, (1986)).

Calculations have shown that a small positive overlap population of 0.024 exists between the two ligands on the unique edge of a $C_{2v}$ capped trigonal prism, indicative of attractive interactions. (Hoffmann et al, *Inorg. Chem.*, 16, 511 (1977)). Such interactions may contribute to the propensity of alkyl isocyanide analogs, for example [Mo(CNR)₆I]⁺, to undergo reductive coupling. (See, Lam et al., *J. Am Chem. Soc.*, 99. 617 (1977); Corfield et al., *Inorg. Chem*, 20, 922 (1981); Dewan et al., *Inorg. Chem.*, 20, 4069 (1981); Giandomenico et al., *J. Am. Chem. Soc.*, 104, 1263 (1982); Carvana et al., *Inorg. Chem.*, 21, 1860 (1982) and Hoffmann et al., *J. Am. Chem. Soc.*, 105, 146 (1983)).

In addition, the low carbonyl infrared stretching frequencies of 1810 and 1747 cm⁻¹ for Compound (5), [Nb(CO)₂(dmpe)₂Cl] and 1833 and 1756 cm⁻¹ for Compound (6), [Ta(CO)₂(dmpe)₂Cl], revealed their electron rich character, another factor associated with the reductive coupling of analogous alkyl isocyanide complexes. (See, Caravana et al., *Inorg. Chem.*, 21, 1860 (1982)).

As described above, two routes to the reductively coupled products have been discovered in this invention. As shown in eq. 3, a reducing agent is first added to a solution (e.g., THF) containing Compound (6). In one route (Method B), the reducing agent is magnesium, activated by $I_2$ or $HgCl_2$, which is followed by addition of a metallocene dihalide as a Lewis acid. Upon stirring at room temperature for several hours, the color changes from yellow to red-brown and the CO stretching bands of Compound (6) disappear and new bands at 1710, 1600, and 1525 cm$^{-1}$ grow in.

These bands were previously postulated to arise from species containing $\eta^2$-CO bridges between Ta and Zr when [(C$_5$Me$_5$)$_2$ZrCl$_2$] was used as the Lewis acid, (Bianconi et al., *J. Am. Chem. Soc.*, 108, 311 (1986)) but several attempts to isolate and structurally characterize this intermediate have proved futile.

Moreover, the present inventors have subsequently been able to generate a very similar solution infrared spectrum using magnesium anthracene and no metallocene dihalide as the reducing agent or by the Mg/HgCl$_2$ method at 45° C. with no added metallocene dihalide. Addition of trimethylsilylchloride to these solutions yields Compound (2).

These results, together with information about the spectroscopic properties of the red-brown intermediate generated by Method A described below, suggest that two of the low frequency infrared bands result from two cis-carbonyl groups in [Ta(CO)$_2$(dmpe)$_2$]$^-$ with solvated Mg$^{2+}$ ions, and not Zr(IV). In Method B, the metallocene dihalides may facilitate electron transfer between magnesium and the tantalum complex, Compound (6).

An attempt to directly use the known complex [(C$_5$Me$_5$)$_2$Zr(N$_2$)](N$_2$) as the reductant produced a purple-red solution which turned green over time without the addition of Me$_3$SiCl. The infrared spectrum showed only the CO bands of the starting material, Compound (6).

In the more preferred second route (Method A), 40% amalgam was used as both reductant and Lewis acid, the latter presumably being solvated Na$^+$ ions. This reaction occurs smoothly for both Compounds (5) and (6) and produces infrared spectral bands at 1750, 1670, and 1600 cm$^{-1}$ for Nb and at 1740, 1675, and 1600 cm$^{-1}$ for Ta. These bands appear to result from two different species since their relative intensities vary with time, the 1750 or 1740 cm$^{-1}$ band first increasing and then diminishing as the reaction proceeds.

This species is presently believed to have the following formula:

trans-[M(CO)$_2$(dmpe)$_2$]

The two low frequency infrared bands grow in continuously with increasing reaction time. While not wishing to be bound by theory, they may be due to the two electron reduction product, cis-[M(CO)$_2$(dmpe)$_2$]$^-$, ion paired with Na$^+$ ions in solution. Addition of tetra(n-hexyl)ammonium chloride to this solution led, in the case where M=Ta, to the formation of red-orange crystals of:

[(n-C$_6$H$_{13}$)$_4$N][Ta(CO)$_2$(dmpe)$_2$]

the crystal structure of which contains the cis-dicarbonylbis(1,2-bis(dimethylphosphino)ethane)-tantalum$^{1-}$ ion A Nujol mull infrared spectrum of this compound exhibited CO stretching bands at 1695 and 1600 cm$^{-1}$.

Once the red-brown solution containing the low frequency carbonyl stretching bands is generated by either Method A or B and filtered, addition of Me$_3$SiY, where Y$^-$=Cl$^-$ or CF$_3$SO$_3^-$, leads to the formation of the desired green, reductively coupled products.

These compounds, which contain the coordinated $\mu_2$-Me$_3$SiOCCOSiMe$_3$ ligand, can be readily identified in solution by their characteristic infrared and $^{31}$P NMR spectra. If one considers the bis(trimethylsiloxy)ethyne ligand to be a 4-electron donor, an assignment consistent with its molecular geometry and $^{13}$C NMR spectrum, (see, Cotton et al., *J. Am. Chem. Soc.*, 101, 5094 (1979); Smith et al., *Inorg. Chem.*, 20, 387 (1981); Templeton et al., *J. Am. Chem. Soc.*, 102, 3288 (1980) and Curtis et al., *Organometallicsm*, 4, 940 (1985)) the products, Compounds (1)–(4) all achieve an 18-electron noble gas configuration. A similar metal-bound trimethylsiloxy ligand occurs in [Fe$_2$(Me$_3$SiOC)$_4$(CO)$_6$]. (See, Nasta et al., *J. Am. Chem. Soc.*, 94, 2449 (1972) and Bennett et al., *J. Am. Chem. Soc.*, 95, 1684 (1973)).

Previous work has shown that the chloride capping ligand in Compound (6) is kinetically inert, and only exchanges by reduction to the [Ta(CO)$_2$(dmpe)$_2$]$^-$ anion followed by oxidative addition of, for example, HX. (See, Datta et al., *Inorg. Chem.*, 16, 1134 (1977)). These observations further support the postulated role of such an anion in the reaction mechanism.

Although the spectroscopic features observed in a mixture of reaction products of eq. 3 had tentatively been assigned to the trimethylsilyl-capped analog:

"[Ta(Me$_3$SiOCCOSiMe$_3$)(dmpe)$_2$(SiMe$_3$)]"

(see, Bianconi et al., *J. Am. Chem. Soc.*, 108, 311 (1986)), the similarity of these spectral properties, especially the 31P NMR spectrum, to those of the iodide-capped complex and the identification of this species as a contaminant in the structure of Compound (3), suggest that the spectral features derive from the iodide-capped coupled ligand product.

Because of its greater simplicity and higher yields, Method A is the preferred route to generate [M(R$_3$SiOCCOSiR$_3$)(dmpe)$_2$Y] complexes. Although the R groups were not varied in reactions using this method, extensive studies using Method B, in which the products were spectroscopically characterized, demonstrated that a variety of silyl halides may be employed.

Specifically, coupled ligand products were observed for Me$_3$SiCl, Ph$_2$MeSiCl, PhMe$_2$SiCl, (t-Bu)Me$_2$SiCl, BzMe$_2$SiCl, and HMe$_2$SiCl but not for (i-Pr)$_3$SiCl, Et$_3$SiCl, or Ph$_3$SiCl. While not wishing to be bound by theory, these results suggest that at least one sterically undemanding lower alkyl group, such as the Me that was present in all successful cases to date, is preferred, possibly for internal packing reasons revealed by the structural studies of Compounds (1)–(4).

Figure 1:
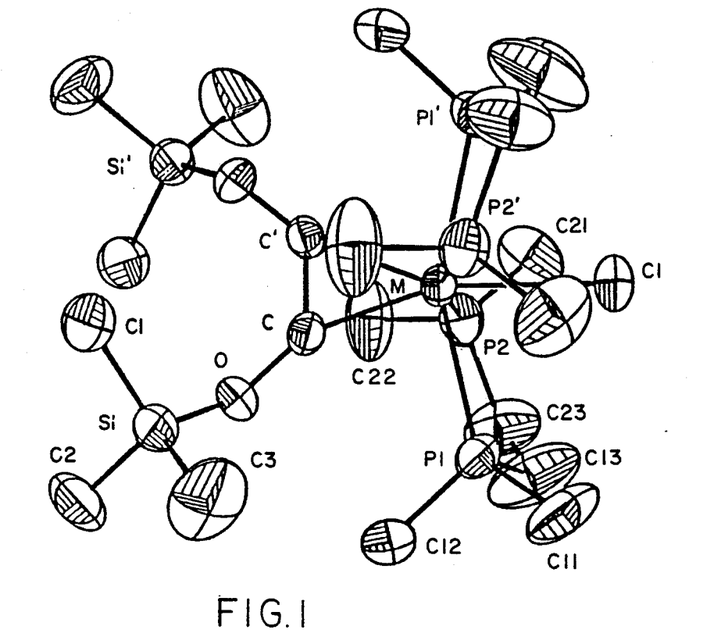
FIG. 1 represents a spatial structure of the isomorphous series of complexes of the present invention, showing the atom labeling scheme and 40% thermal ellipsoids for Compound (2). These compounds have the generic structure.

The structure of [Ta(Me$_3$SiOCCOSiMe$_3$)(dmpe)$_2$Cl] is shown in FIG. 1. All three members of the isomorphous series of Compounds (1)–(3) lie on a crystallographically required two-fold symmetry axis that passes through the metal, halide, and midpoint of the C—C bond of the acetylene diether ligand.

Figure 2:
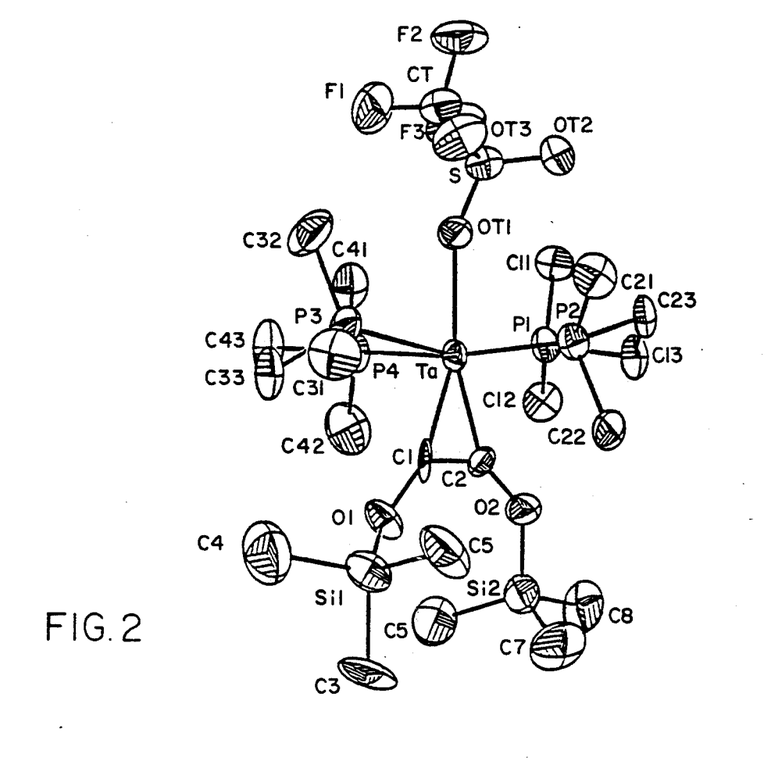
FIG. 2 represents the structure of Compound (4), [Ta(Me₃SiOCCOSiMe₃)(dmpe)₂(OSO₂CF₃)], showing the 40% thermal ellipsoids and atom labeling scheme.

The triflate analog, Compound (4) has a similar structure (see, FIG. 2) but only C$_1$ point group symmetry. The coupled ligand and the halide or triflate anion are trans to one another in the coordination sphere, which is completed by two chelating 1,2-bis(dimethylphosphino)ethane ligands in the equatorial positions.

When viewed down the Ta-Y bond axis, it is apparent that the metal centers in Compound (2) (see, FIG. 3) and its analogs are chiral, a feature that could ultimately prove valuable in achieving the synthesis of optically active products by subsequent reaction chemistry of Compounds (1)–(4) and related molecules.

The Ta-Cl and Ta-P bond distances of Compounds (1)-(4) are similar to those found in the [Ta(CO)$_2$(dmpe)$_2$Y] starting materials, (see, Bianconi Ph.D. Thesis, Massachusetts Institute of Technology, 1986) in [Ta($\eta^4$-anthracene)(dmpe)$_2$Cl], (ibid.), and in [Ta($\eta^4$-naphthalene)(dmpe)$_2$Cl], (see, Albright et al., *J. Am. Chem. Soc.*, 101, 611 (1979)). They are not longer than the values found in the lower coordinate, higher oxidation state molecule [Ta(dmpe)$_2$Cl$_2$]. The Ta—I bond length of 2.90 Å found for the 20% impurity of [Ta(Me$_3$SiOCOSiMe$_3$(dmpe)$_2$Cl$_{0.8}$I$_{0.2}$] in Compound (3) is 0.32 Å longer than the Ta-Cl distances in Compounds (2) and (3), in excellent agreement with the known difference of 0.34 Å in Cl and I covalent radii. (See, L. Pauling in "The Nature of the Chemical Bond, 3rd ed."; Cornell University Press, Ithaca, N.Y., p. 224 (1960)). Similar bond length variations occur in related seven-coordinate Mo and W complexes. (See, Lews et al., *Inorg. Chem.*, 11, 621 (1982); Drew et al., *J. Chem. Soc. Dalton Trans.*, 2664 (1973); Drew et al., *Acta Cryst.*, 33B, 1027 (1977); Lam et al., *Inorg. Chem.*, 17, 2127 (1978); Szalda et al., *Inorg. Chem.*, 20, 3851 (1981); Burgmayer et al., *Inorg. Chem.*, 24, 2224 (1985) and Fong et al., *Inorg. Chem.*, 25, 1880 (1986)). The Ta-O bond length of 2.293 Å in the triflate analog, Compound (4) is 0.28 Å shorter than the Ta-Cl distance in Compound (2), a difference also expected on the basis of the covalent radii of oxygen (0.66 Å) and chlorine (0.99 Å).

The chelating dmpe groups in the equatorial plane are puckered and tipped in the direction of the axial (Y) ligands, halide or triflate, owing to steric interactions with the more bulky alkyne ligand. The metal therefore lies out of the mean plane through the four phosphorus atoms, by 0.441, 0.453, 0.449 and 0.274 Å, respectively, for Compounds (1)-(4). These values are consistent with the fact that the triflate ion is sterically more demanding than the chloride ion.

Similar conclusions can be drawn from the dihedral angles (alpha) about the C—C bonds of dmpe chelate rings, which are less puckered (alpha=25.4°, 32.4°, and 32.1°) for Compounds (1), (2), and (3) than for Compound (4) (alpha=47.2° and 52.7°). The different steric demands of the chloride and triflate anions are further revealed by the dihedral angles between planes defined by P—M—P groups which are nearly identical for Compounds (1), (2), and (3) (26.0°, 27.1°, and 26.8°), are smaller by about 10° in the case of Compound (4) (17.2°) as a consequence of the greater steric bulk of triflate compared to chloride.

All five-membered metal-dmpe chelate rings exhibit half chair (C$_2$) conformations, (E. L. Eliel, In "Stereochemistry of Carbon Compounds", McGraw Hill: New York, N.Y., chapter 9, 1962) where the two-fold axis passes through a phosphorus atom and the midpoint of opposite bond, except for one of the rings in Compound (4) (Ta-P1-Cl3-C23-P2), where the two-fold axis passes through the metal and the midpoint of the bond between the methylene carbon atoms.

Figure 3A:
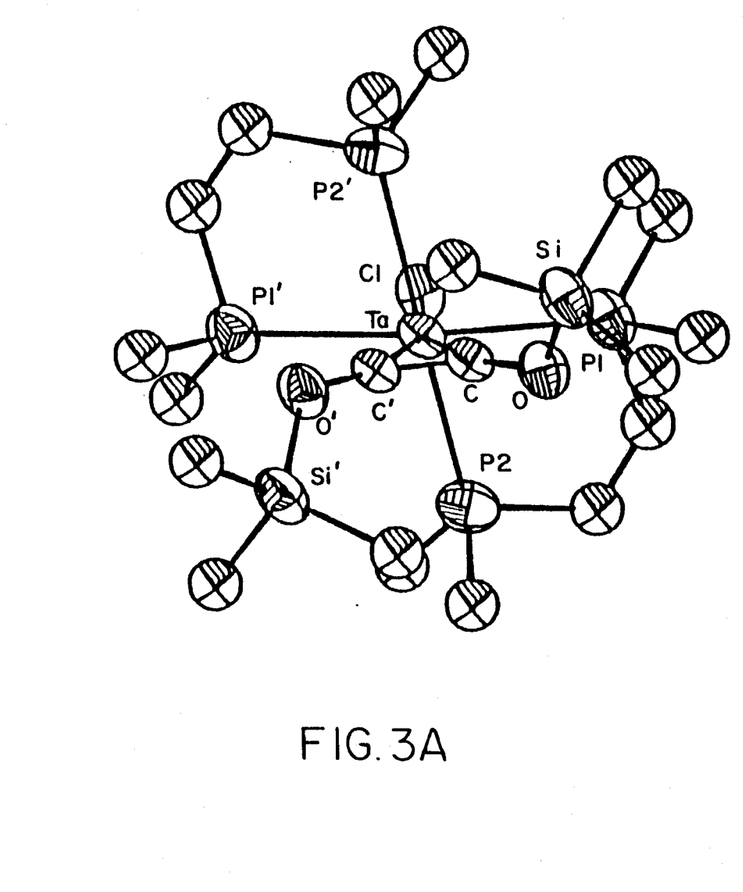
FIG. 3 is a comparison of the structures of (A), [Ta(Me₃SiOCCOSiMe₃)(dmpe)₂Cl], Compound (3), and (B), [Nb(CO)₂(dmpe)₂Cl], Compound (5), viewed approximately down their molecular $C_2$ axes.
Figure 3B:
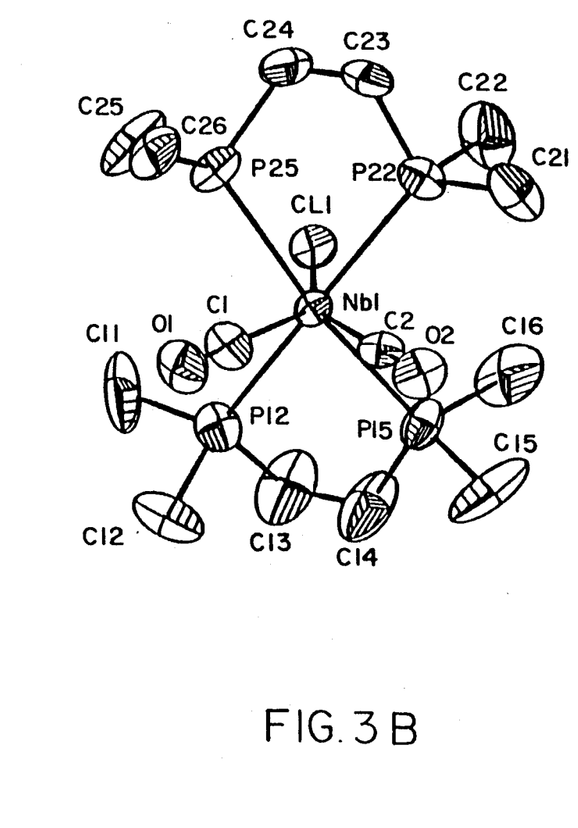

Comparison of the molecular structures of Compounds (1)-(4) with those of Co mounds (5) and (6), the seven-coordinate niobium and tantalum starting materials, reveals that the coordination geometry of the metals undergoes subtle changes upon reductive coupling (see, FIG. 3).

The metal atoms of Compounds (1)-(4) are more displaced from the best planes through the P$_4$ atoms (toward the alkyne ligand, see above) than is the case for Compounds (5) and (6) (about 0.36 Å), reflecting possibly the greater stearic demands of the bulky SiMe$_3$ groups of the coupled complex.

A more significant change in the Nb or Ta coordination sphere upon reductive coupling, however, is the orientation of the C—C vector. As shown in FIG. 3, the C—M—C planes in Compounds (5) and (6) are staggered with respect to the M—P bond axes, resulting in nearly perfect C$_{2v}$ capped trigonal prismatic geometry. In Compounds (1)-(4), the C—C bonds are twisted by 45°, so that they are aligned parallel to one of the P-Ta-P vectors, making the D$_{5h}$ pentagonal bipyramid the closest seven-coordinate idealized reference polyhedron. (See, Szalda et al., *Inorg. Chem.* 20, 3851 (1981)).

The pentagonal plane (FIG. 3) is formed by C, C', P1, P1'; and C1 (all deviations <0.05 Å); the atypical ligands are P2 and P2'; and the P2-M-P2' angle is 164.1°. Similarly distorted pentagonal bipyrimidal geometry was seen in [Ta$\eta^4$-naphthalene)(dmpe)$_2$Cl] and [Ta($\eta$-$^4$anthracene)(dmpe)$_2$Cl]. (See, Bianconi Ph.D. Thesis, Massachusetts Institute of Technology, 1986). Inspection of bond angles at the metal center confirms that the pentagonal bipyramid is the best seven-coordinate geometric assignment for Compounds (1)-(4), with appreciable distortions from idealized pentagonal bipyramidal geometry being mainly due to the presence of three chelating ligands.

The eclipsed ligand conformation just described for Compounds (1)-(4) may be adopted in the solid state in order to place the bulky trimethylsilyl groups in the sterically least demanding position between the dmpe ligands. Electronic factors involving attainment of the best overlap of metal d and alkyne pi-orbitals may also be involved, however, as was found to be the case in the solid state geometries of some other high-coordinate complexes with pi-accepting ligands. (See, Burgmayer et al., *Inorg. Chem.*, 24, 2224 (1985)).

The NMR spectra of Compound (2) are also consistent with the assignment of the bis(trimethylsiloxy)ethyne ligand as a 4e$^-$ donor. The $^1$H, $^{13}$C and $^{31}$P NMR chemical shifts are almost unchanged from those of Compound (6), the uncoupled starting material; the one large difference is in the position of the $^{13}$C resonance of the coupled CO ligands. These resonances occur at 273 ppm for Compound (6) and experience a 60 ppm upfield shift, to 212 ppm, for Compound (2). Also, a phosphorus-carbon coupling of 15 Hz is observed for the alkyne carbons of Compound (2), resulting in a quintet, while the CO carbons of Compound (6) appear as a singlet in the $^{13}$C NMR spectrum The position of the $^{13}$C resonance of the alpha-carbons of bound alkynes has been used to assign them as 4e$^-$, 3e$^-$, or 2e$^-$ donors (See, Templeton et al., *J. Am. Chem. Soc.*, 102, 3288 (1980) and Curtis et al., *Organometallics*, 4, 940 (1985)). By this criterion, Compounds (2)-(4) are 4e$^-$ donors.

Figure 4A:
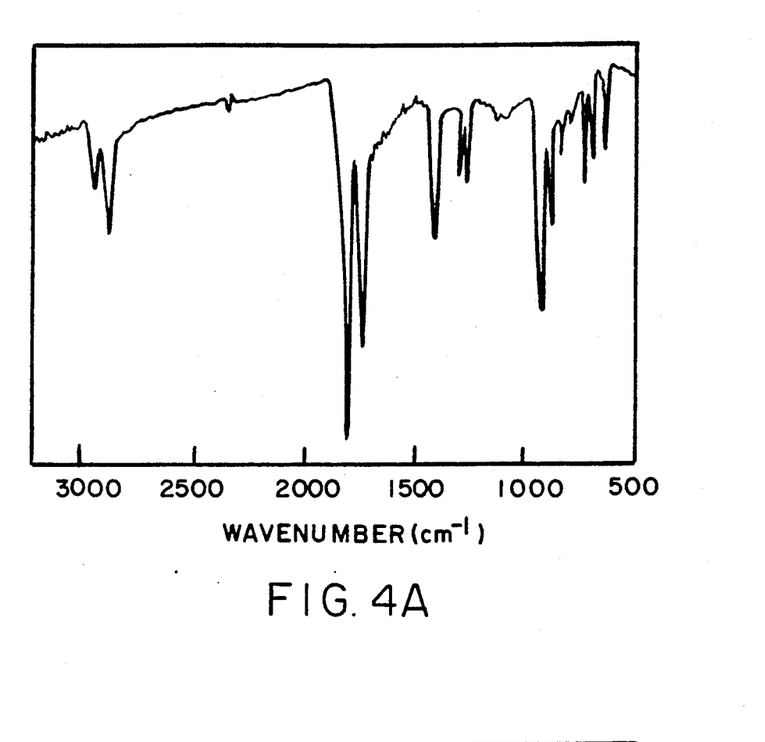
FIG. 4 is the FTIR spectra of (a), Compound (6), [Ta(CO)₂(dmpe)₂Cl] and (b), Compound (2), [Ta(Me₃SiOCCOSiMe₃)(dmpe)₂Cl], in KBr pellets.
Figure 4B:
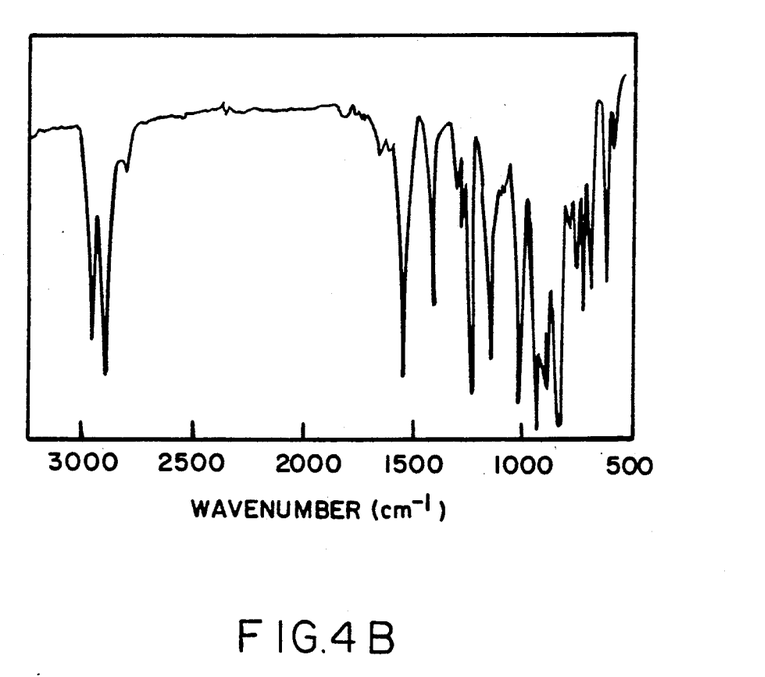

Both the structural and spectroscopic properties of the coupled ligands of Compounds (1)-(4) much more closely resemble those of the alkyne ligands derived from the reductive coupling of isocyanides than those of any other ligand derived from reductive coupling of CO. In the IR spectra of both the coupled CNR and CO complexes a new, medium-to-strong band, characteristic of the coupled ligand, appears. In the CNR case, this peak occurs between 1584 and 1687 cm$^{-1}$ In the CO case, it falls about 1540 cm$^{-1}$, while the two strong terminal CO stretching bands in the starting Compound (6) disappear (see, FIG. 4). This 1540 cm$^{-1}$ band is attributed to the C≡C or C≡O stretches of the coupled ligand.

Only the tantalum species, Compounds (2)–(4) were analyzed by $^{31}$P NMR spectroscopy, since the large quadrupole moment associated with the niobium ($^{93}$Nb) nucleus causes severe broadening of the signals of Compound (1). The $^{31}$P NMR spectrum of Compound (2) consists of a singlet at 25.0 ppm, while in Compound (4) the peak shifts to 27.8 ppm. In the iodide-capped impurity in Compound (3), the resonance occurs at 14.0 ppm. The equivalence of the four phosphorus sites is also revealed by their equivalent coupling to the alkyne carbon atoms. The $^1$H and $^{13}$C NMR spectra also demonstrate that, in solution, Compounds (2)–(4) have effective $C_{2v}$ symmetry. Only one resonance appears for the dmpe methylene carbon atoms, and the dmpe methyl carbon atoms form two distinct sets, those directed towards the capping ligand and those directed towards the alkyne, as is seen in Compound (6) and other capped trigonal prismatic compounds containing the two equatorial chelating dmpe groups.

The fluxional process which may best account for the solution NMR spectra of Compounds (2)–(4) is rotation of the alkyne ligand around the Ta-Cl vector. Low temperature $^{13}$C and $^{31}$P NMP show this to be true. This fluctional process is seen down to $-90°$. This process occurs in at least two other seven-coordinate complexes containing a n-accepting chelating ligand, specifically, [Mo(CN-t-Bu)$_5$(t-Bu-HNCCNH-t-Bu)][BPh$_4$]$_2$ and [Ta($\eta^4$-naphthalene)-(dmpe)$_2$Cl]. (See, Bianconi Ph.D Thesis, Massachusetts Institute of Technology, 1986; and Albright et al., *J. Am. Chem. Soc.*, 101, 611 (1979)).

$^{31}$P NMR spectra taken at various intervals during the reduction of Compound (6) with Na(Hg) show four signals at 32.3, 22.4, 11.6 and 7.9 ppm during the initial stages of the reduction. Two of these disappear as the reaction proceeds, leaving the two at 22.4 and 7.9 ppm, which are known to be those of [Ta(CO)$_2$(dmpe)$_2$]$^-$. Since addition of Me$_3$SiCl to this latter species generates Compound (2), $^{31}$P NMR spectroscopy should prove to be useful in future mechanistic studies of eq. 3.

Another preferred embodiment of the present invention involves the chemistry leading to the formation of the dihydroxyacetylene molecule stabilized by coordination to tantalum in [TaH(HOCCOH)(dmpe)$_2$Cl]$^+$, Compound (8).

When [Ta(Me$_3$SiOCCOSiMe$_3$)(dmpe)$_2$Cl], Compound (2), dissolved in THF was allowed to react under nitrogen with one equivalent of HCl as a 7.6% aqueous solution, there was a rapid color change from dark green to pale yellow. After thirty minutes, white microcrystals of [TaH(HOCCOH)(dmpe)$_2$Cl]Cl, Compound (7), formed which were isolated by filtration and washed with THF (yield 94%). This reaction also can be accomplished by adding two equivalents of distilled water or excess methanol, thereby providing the necessary protons or acidic conditions, for reaction of Compound (2), but with significantly lower isolated yields (<50%).

Figure 5:
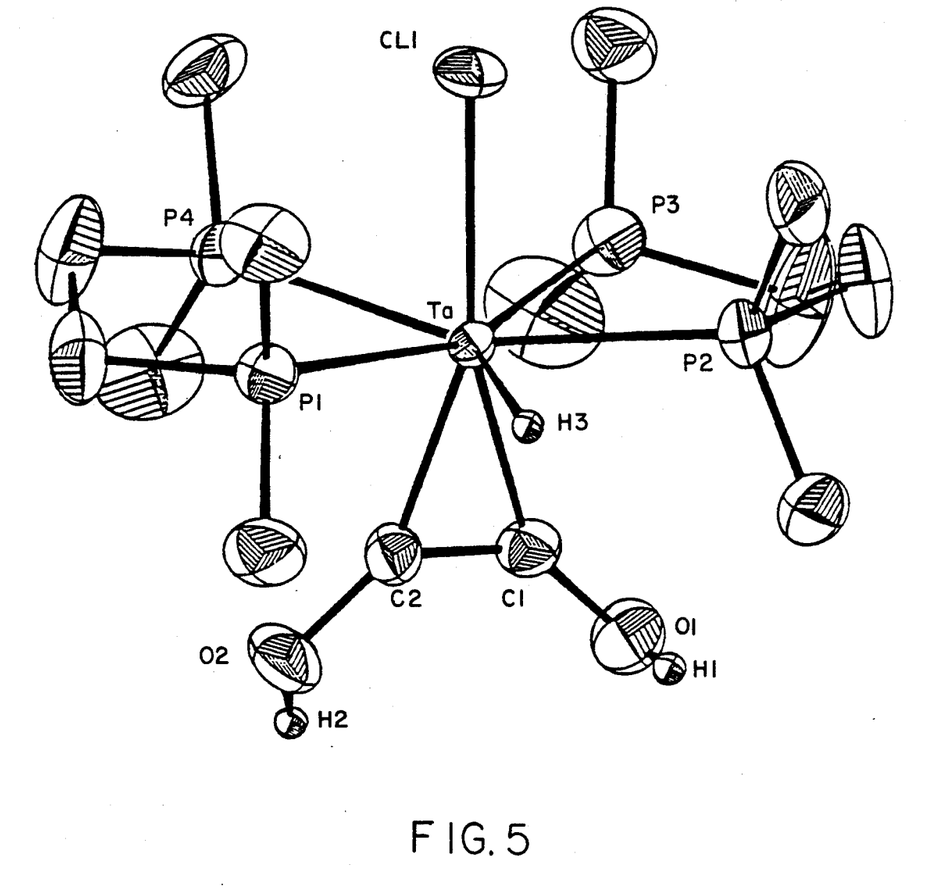
FIG. 5 represents the spatial structure of Compound (7) showing the 40% thermal ellipsoids and atom labeling scheme.

FIG. 5 displays the structure of Compound (7) along with some geometric information. Compound (7) is the first example of a structurally characterized molecule with a dihydroxyacetylene ligand. The coordination geometry of tantalum is pentagonal-bipyramidal, with the chloride atom and the midpoint of the dihydroxyacetylene ligand in axial positions. The equitorial plane contains a hydride and two chelating dmpe ligands.

The geometry about the HO—C≡C—OH ligand is similar to that of other 4-electron donating alkyne complexes of tantalum. See, Leutkins et al., *Inorg. Chem.*, 26, 2430 (1987). The hydroxyl protons on the dihydroxyacetylene ligand were located directly from difference Fourier maps and refined. The hydride atom was also located on the difference Fourier maps in what appeared to be two disordered positions. Refinement of the hydrogen at the position of greater electron density resulted in a Ta-H distance of 1.89(14) Å. This value may be compared with average distances of 1.80(1) Å and 1.774(3) Å reported in neutron diffraction structures of [TaClH$_2$(PMe$_3$)$_4$] and [Cp$_2$TaGH$_3$] (Leutkins et al., *J. Amer. Chem. Soc.*, 105, 4474 (1983)) and 1.94(11) and 1.85(11) Å found in the X-ray diffraction structure of [TaCl$_2$H$_2$(PMe$_3$)$_4$] (Meakin et al., *Inorg. Chem.*, 13, 1025 (1974)).

A trans influence of the hydride ion results in a 0.08 Å lengthening in the average Ta-P bond lengths of the trans-phosphines [P(3) and P(4), 2.632(8) Å]versus that for the cis-phosphines [P(1) and P(2), 2.552(4) Å]. This effect can also be seen in the $^{31}$P NMR spectrum of the cation, Compound (8). The $^{31}$P{$^1$H} NMR spectrum of (8) consists of two resonances at 14.55 and 35.45 ppm. When the spectrum is run without proton decoupling, however, the downfield resonance splits into a doublet with a $^2$JPH=90 Hz. Similar behavior occurs in the $^{31}$P NMR spectrum of [TaH(CO)$_2$(dmpe)$_2$] which has a hydride-capped octahedral structure with trans-CO ligands.

When a small amount of D$_2$O is added to a solution of Compound (8) in CDCl$_3$, the hydroxyl protons at 11.0 ppm in the $^1$H NMR spectrum disappear while the hydride resonance, which appears as a triplet of triplets at 5.1 ppm does not change. The exchangeability of these two protons was also observed in a FAB mass spectrometry experiment of which some D$_2$O was added to the matrix containing Compound (8) prior to bombardment.

Although no mechanistic information is yet available, the reaction is formally comprised of two steps. One is protiolysis by water or HCl to yield the dihydroxyacetylene ligand along with bis(trimethylsilyl)ether, trimethylsilanol, or trimethylsilyl chloride. The other involves reaction with HCl in an oxidative addition step. The sequence of these two steps is currently being investigated. When no HCl is added, it could be formed in situ by hydrolysis of a Ta-Cl bond. Although no hydrolysis products containing a Ta-OH bond have yet been identified, a yellow, THF-soluble compound forms in reactions of Compound (2) with distilled water or methanol which may contain such a species. In what may be a similar reaction, the compound [Fe$_2$(Me$_3$SiOC)$_4$(CO)$_3$], which contains metallocyclopentadiene fragment, reacts with anhydrous HCl releasing two equivalents of Me$_3$SiCl. Partial characterization of the product revealed the presence of —OH functionalities, but further details have not been reported.

In summary, the reaction of [Ta(Me$_3$SiOCCOSiMe$_3$)(dmpe)$_2$Cl](2) under appropriate acidic conditions, produces a tantalum complex containing the novel dihydroxyacetylene ligand, [TaH(HOCCOH)(dmpe)$_2$Cl]Cl (7). Since Compound (7) is much more stable than (2) it may be an important precursor for further transformations of the alkyne moiety.

EXAMPLES

The present invention will be further illustrated with reference to the following examples which aid in the understanding of the present invention, but which are not to be construed as limitations thereof. All temperatures are expressed in degrees Celsius.

MATERIALS

All reactions and manipulations were carried out under nitrogen, using standard Schlenk techniques or a Vacuum Atmosphere dry box. Solvents were distilled under nitrogen from sodium benzophenone ketyl an stored over molecular sieves. Deuterated benzene was dried by passage through a column of alumina and stored over 3 Angstrom molecular sieves.

Compound (5), [Nb(dmpe)$_2$(CO)$_2$Cl] and Compound (6), [Ta(CO)$_2$(dmpe)$_2$Cl] were synthesized by using modified literature procedures (see, Bianconi, Ph.D. Thesis, Massachusetts Institute of Technology, (1986); and Datta, et al., *Inorg. Chem.* 16, 1134 (1977)).

Forty percent sodium amalgam was prepared by the literature method of Fieser, et al., "Reagents for Organic Synthesis"; John Wiley & Sons: New York, vol. 1, p. 1033 (1967).

Chlorotrimethylsilane (Me$_3$SiCl) (Aldrich, Petrarch); trimethylsilyltrifluoromethanesulfonate (Me$_3$SiCF$_3$SO$_3$) (Aldrich); magnesium (J. T. Baker); and [C$_5$Me$_5$)$_2$ZrCl$_2$] (Strem); were obtained from the named commercial sources and used without further purification.

[(C$_5$Me$_5$)$_2$Zr(N$_2$)]2(N$_2$) was provided by Prof. J. A. Bercaw. Tetraethylammonium chloride (Et$_4$NCl) and tetra-n-hexyl-ammonium chloride [(C$_6$H$_{13}$)$_4$NCl]salts (Aldrich) were dried by heating them at 100° C. under vacuum for 5-6 days.

SPECTRAL MEASUREMENTS

The $^1$H and $^{13}$C NMR spectra were recorded on Bruker WM-250 and WM-270 MHz and/or Varian 300 and 400 MHz instruments. $^{31}$P NMR spectra were measured on a JEOL-FX 90 spectrometer and referenced to external 85% H$_3$PO$_4$. The $^{19}$F NMR spectrum was obtained on the same instrument, using fluorobenzene (delta -113.1) as an internal standard; the reported $^{19}$F chemical shifts are referenced to CFCl$_3$. Infrared (IR) spectra were recorded on a Beckman Acculab 10 grating or IBM IR/30S FTIR spectrometer. Electronic spectra were measured in the region 250-800 nm on a Perkin-Elmer Lambda 7 UV-visable spectrophotometer. Elemental analyses were performed by Galbraith Laboratories, Knoxville, Tenn.

EXAMPLE 1

PREPARATION OF COMPOUND (1)
[Nb(Me$_3$SiOCCOSiMe$_3$)(dmpe)$_2$Cl]

A mixture containing [Nb(CO)$_2$(dmpe)$_2$Cl] [Compound (5)](0.1179 g, 0.243 mmol), 40% sodium amalgam (0.958 g), and 6 mL of THF was stirred in a 25 mL flask for 24 h, during which time the color changed from orange to red-brown. The IR spectrum of the filtered solution displayed three CO stretching bands at 1750, 1670, and 1600 cm$^{-1}$. Addition of 0.090 mL of Me$_3$SiCl (0.71 mmol) to the filtered solution produced an immediate color change from red-brown to plum red. After an additional 3 h of stirring, the color of the reaction mixture turned to dark green and the THF was removed in vacuo.

The green product was then extracted into pentane which, upon cooling to −30° C., yielded 0.103 g (67%) of crystalline [Nb(Me$_3$SiOCCOSiMe$_3$)(dmpe)$_2$Cl], Compound (1).

Analytical data: IR (KBr pellet) 2958 (w), 2896 (m), 2800 (w), 1557 (m), 1421 (w), 1292 (w), 1277 (w), 1258 (sh), 1246 (m), 1140 (m), 1003 (m), 939 (s), 924 (sh), 890 (s) 846 (s), 758 (w), 725 (m), 694 (m), 628 (m), 594 (w), 450 (w) cm$^{-1}$. UV-vis (THF, 1.41 mM) 322 nm (11,000 M-1 cm$^{-1}$), 448 (sh), 641 (90).

Anal Calcd. for C$_{20}$H$_{50}$ClO$_2$P$_4$Si$_2$Nb: C, 8.07; H, 7.99; Cl, 5.62. Found: C, 38.04; H, 8.07; Cl, 5.66.

EXAMPLE 2

PREPARATION OF COMPOUND (2)
Ta(Me$_3$SiOCCOSiMe$_3$)(dmpe)$_2$Cl]

Method A

A mixture of Compound (6), [Ta(CO)$_2$(dmpe)$_2$Cl] (0.114 g, 0.199 mmol), 40% sodium amalgam (0.65 g), and 5 mL of THF was stirred in a 25 mL flask for 8 h, during which time the solution changed its color from orange to red-brown. The IR spectrum of the solution phase of this mixture consisted of three CO stretching bands at 1740, 1675, and 1600 cm$^{-1}$. To the filtered mixture, Me$_3$SiCl (0.065 mL, 0.512 mmol) and Et$_4$NCl (0.034 g, 0.205 mmol) were added, resulting in an immediate color change from red-brown to plum-red. After an additional 5 h of stirring, the color of the solution became dark green.

The THF solvent was removed in vacuo and the green product extracted into 4 mL of pentane which, upon cooling to −30° C., yielded 0.096 g (67%) of Compound (2), [Ta(Me$_3$SiOCCOSiMe$_3$)(dmpe)$_2$Cl].

Analytical Data: $^{31}$P {$^1$H} NMR (36.6 MHz, pentane) delta 24 (s); IR (KBr pellet) 2959 (w), 2897 (m) 2800 (w), 1547 (m), 1420 (w), 1290 (w), 1277 (w), 1258 (sh), 1248 (m), 1144 (m), 1015 (m), 938 (s), 924 (sh), 899 (m), 845 (s), 756 (w), 727 (m), 692 (w), 625 (w) cm$^{-1}$; UV-vis (THF, 1.341×10$^{-4}$M) 329 nm (12,400 M$^{-1}$cm$^{-1}$), 438 (sh), 580 (109).

Anal. Calcd. for C$_{20}$H$_{50}$ClO$_2$P$_4$Si$_2$Ta: C, 33.41; H, 7.01; Cl, 4.93. Found C, 33.10; H, 6.40; Cl, 5.00.

This reaction was subsequently reproduced without the addition of Et$_4$NCl.

EXAMPLE 3

PREPARATION OF COMPOUND (2)
[Ta(Me$_3$SiOCCOSiMe$_3$)(dmpe)$_2$Cl]

Method B

Mg dust (1.0 g, 41 mmol) and HgCl$_2$ (1.37 g, 5 mmol) were stirred in 30 mL of THF and warmed slightly above room temperature for 5-10 min. After the addition of Compound (6), [Ta(CO)$_2$(dmpe)$_2$Cl] (0.573 g, 1 mmol) and [(C$_5$Me$_5$)$_2$ZrCl$_2$] (0.432 g, 1 mmol), the reaction mixture was stirred at room temperature and monitored by solution IR. After a 3-12 hr period of stirring, the CO stretching vibrational bands of Compound (6) completely disappeared and new bands at 1710, 1600, and 1525 cm$^{-1}$ grew in.

The reaction mixture was filtered and the filtrate was treated with Me$_3$SiCl (0.254 mL, 2 mmol) at −78° C. The solution turned green upon warming to room temperature and stirring for 12 h. Removal of the solvent in vacuo, extraction of the residue with 40 mL of pentane, filtration, reduction of the volume of the filtrate to 4 mL, and cooling to −20° C. resulted in the formation of 0.18 g (25%) of Compound (2), [Ta(Me$_3$SiOCCOSiMe$_3$)(dmpe)$_2$Cl].

Analytical Data: $^1$H NMR (250 MHz, C$_6$D$_6$) delta 1.51, 1.47 (s, PCH$_3$), 0.24 (s, SiCH$_3$); $^{13}$C [$^1$H]NMR (67.9 MHz, C$_6$D$_6$) delta 2.20 (SiMe$_3$), 18.4, 9.5 (PCH$_3$), 33.6 (t, J$_{C-P}$=8 Hz, PCH$_2$), 212.5 (quintet, J$_{C-P}$=15 Hz, COSiMe$_3$); $^{31}$P {$^1$H} NMR (THF) delta 25.0 (s); IR (Nujol mull) 1540 (m), 1420 (m), 1298 (w), 1280 (w), 1260 (sh), 1250 (s), 930 (s), 910 (m, br), 850 (s), 760 (w), 730 (m), 700 (m), 630 (m) cm$^{-1}$.

Anal. Calcd. for C$_{20}$H$_{50}$Cl$_{02}$P$_4$Si$_2$Ta: C, 33.41; H, 7.01; Cl, 4.93. Found: C, 32.7; H, 6.63; Cl, 4.63.

EXAMPLE 4

PREPARATION OF COMPOUND (3)
[Ta(Me$_3$SiOCCOSiMe$_3$)(dmpe)$_2$Cl$_{0.8}$I$_{0.2}$]

Mg dust (1.0 g, 41 mmol) and I$_2$ (50–80 mg, 0.20–0.32 mmol) were stirred and warmed slightly above room temperature in 30 mL of THF until the solution was colorless (about 5 min). Compound (6), [Ta(CO)$_2$(dmpe)$_2$Cl] (0.573 g, 1 mmol) and [(C$_5$Me$_5$)$_2$ZrCl$_2$](0.432 g, 1 mmol), were added and the reaction mixture was stirred at room temperature and monitored by solution IR. After a 3–12 hr period of stirring, the CO stretching vibrational bands of Compound (6) completely disappeared and new bands at 1710, 1600, and 1525 cm$^{-1}$ grew in.

The reaction mixture was filtered and the filtrate was treated with Me$_3$SiCl (0.254 mL, 2 mmol) at −78° C. The solution turned green upon warming to room temperature and stirring for 12 h. Removal of the solvent in vacuo, extraction of the residue with 40 mL of pentane, filtration, reduction of the volume of the filtrate to 4 mL, and cooling to −20° C. resulted in the formation of 0.366 g of green crystals. This product was found to be a mixture of two compounds, based upon solution spectroscopic data. These products could not be separated by fractional crystallization from pentane, methylene chloride, benzene, toluene, ether, or mixtures thereof; and they decomposed when chromatographed on alumina or silica gel. They could not be distinguished by their crystal habits.

Analytical Data: $^1$H NMR (250 MHz, C$_6$D$_6$) delta 1.78, 1.51, 1.49, 1.47 (s, PCH$_3$), 0.24, 0.22 (s, SiCH$_3$); $^{13}$C [$^1$H]NMR (C$_6$D$_6$) delta 2.20 (s, SiCH$_3$), 11.7 (br, m, SiCH$_3$, 24.5, 19.5, 18.4, 17.8 (s, br, PCH$_3$), 34.9, 33.6 (t, $^{2J}$ C-P=9 Hz, PCH$_2$), 212.5, 211.6 (quintet, $^2$J$_{C-P}$=15 Hz=COSiMe$_3$); $^{31}$P [$^1$H] NMR (THF) delta 14.0, 25.0; IR (Nujol mull): 1540 cm$^{-1}$.

EXAMPLE 5

PREPARATION OF COMPOUND (4)
[Ta(Me$_3$SiOCCOSiMe$_3$)(dmpe)(OSO$_2$CF$_3$)]

A mixture of Compound (6) (0.11 g, 0.192 mmol), 40% sodium amalgam (0.714 g), and 6 mL of 1,2-dimethoxyethane (glyme) was stirred in a 25 mL round bottomed flask for 12 hr, during which time the color changed from orange-yellow to red-brown.

The IR spectrum of the solution component of this mixture showed three CO stretching bands at 1740, 1675, and 1600 cm$^{-1}$. The mixture was then filtered, and to the filtrate Was added 0.090 mL (0.466 mmol) of Me$_3$SiOSO$_2$CF$_3$. The solution immediately turned to green, but was allowed to stir for an additional period of 5 hr.

The glyme was then removed in vacuo and the green product extracted into 4 mL of pentane which, upon cooling to −30° C., yielded 0.0629 g (39%) of Compound (4), [Ta(Me$_3$SiOCCOSiMe$_3$)(dmpe)$_2$(OSO$_2$CF$_3$)].

Analytical Data: $^{31}$P [$^1$H]NMR (pentane) delta 28.8 (s); $^{19}$F NMR (pentane) delta -77.8 (s); IR (KBr pellet) 2966 (w), 2898 (m), 2805 (m), 1575 (br, m), 419 (m), 1316 (s), 1248 (s), 1233 (s), 1206 (s), 1180 (s), 1146 (s), 1031 (sh), 1013 (s), 935 (s), 900 (m), 847 (s), 788 (m), 755 (m), 698 (m), 629 (s), 582 (w), 518 (w), 507 (w), 450 (w) cm$^{-1}$ UV-vis (THF, 1.33 mM) 328 nm ($\epsilon$=12,000 M$^{-1}$ cm$^{-1}$), 458 (sh), 608 (160).

Anal. Calcd. for C$_{21}$H$_{50}$F$_3$O$_5$P$_4$SSi$_2$Ta: C, 30.29; H, 6.05; S, 3.85. Found: C, 29.95; H, 6.16; S, 3.83.

EXAMPLE 6

X-RAY DATA FOR COMPOUND (1)
[Nb(Me$_3$SiOCCOSiMe$_3$)(dmpe)$_2$Cl]

Green, parallelepipeds were obtained directly by slow evaporation of the pentane extract of the reaction mixture (see above) at −30° C. Since these crystals were large compared to the size required for X-ray purposes and were also extremely air sensitive, they were reduced in volume, mounted in 0.5 mm Lindemann glass capillaries with a protective coating of a thin layer of light element Apiezon grease, and studied on the diffractometer.

The crystal used for data collection showed acceptable mosaic spread and no fine structure as checked through the open counter ω-scans of several strong, low-angle reflections ($\omega_{\frac{1}{2}}$=0.19°). The Laue symmetry (2/m) and the systematic absences (hkl, h+k+l=/=2n; h0l, h, l=/=2n) revealed a body centered monoclinic lattice consistent with either a centrosymmetric, I2/a (non-standard setting of C2/c, No. 15), or a noncentrosymmetric, Ia (non-standard setting of Cc, No. 9), space group. (See, Hahn, T., Ed. "International Tables for Crystallography"; D. Reidel: Dordrecht, pp. 140, 182 (1983)).

The subsequent successful determination and refinement of the structure indicated the centrosymmetric space group to be the correct one. Since there were no well-defined faces for the crystal used for data collection, an empirical absorption correction was applied.

Further experimental details of data collection and reduction are presented in Table I.

EXAMPLE 7

X-RAY DATA FOR COMPOUND (2)
[Ta(Me$_3$SiOCCOSiMe$_3$)(dmpe)$_2$Cl]

Red-green crystals of Compound (2) were grown and mounted as described for Compound (1) in Example 5. A crystal with acceptable ω-scans was used for data collection and found to be isomorphous with Compound (1). The structure determination and refinement were carried out in space group I2/a. Since three intensity standard reflections measured after every 1 hr. of exposure showed 13% decay over the course of data collection, a linearly interpolated fall-off correction was applied. Absorption corrections were made as described for Compound (1). Experimental details are presented in Table I.

EXAMPLE 8

X-RAY DATA FOR COMPOUND (3)
[Ta(Me$_3$SiOCCOSiMe$_3$)(dmpe)$_2$Cl$_{0.8}$I$_{0.2}$]

This compound was obtained from a reaction where I$_2$ was used to activate magnesium as described above. Crystals were grown as described for Compound (1) and mounted in capillaries.

Data collected on an acceptable crystal showed Compound (3) to be isomorphous with Compounds (1) and (2). Intensity standards decayed by 37% linearly with time during the collection of data, which were corrected accordingly. An analytical absorption correction was applied. Experimental details of data collection and reduction are presented in Table I.

EXAMPLE 9

X-RAY DATA FOR COMPOUND (4)
[Ta(Me$_3$SiOCCOSiMe$_3$)(dmpe)$_2$(OSO$_2$CF$_3$)]

Red-green crystals were grown by slow evaporation of a pentane extract of the reaction residue at $-30°$ C.. Selection, manipulation and handling of the crystals were as described for Compound (1). The crystals exhibited acceptable diffraction quality ($\omega_{178}=0.15-0.20°$) with no fine structure. Study on the diffractometer revealed 2/m Laue symmetry and systematic absences (h0l, 1 =/=2n; 0k0, k=/=2n), consistent with space group P2$_1$/c (C$^5_{2h}$, No. 14). (See, T. Hahn, Ed. "International Tables for Crystallography" D. Reidel Dordrecht, p. 174, (1983)). A linear fall-off correction was applied to compensate for the observed 14% decay of standard reflections during data collection. Further details of the data collection and reduction are given in Table I.

EXAMPLE 10

STRUCTURE DETERMINATION AND REFINEMENT COMPOUND (1)
[Nb(Me$_3$SiOCCOSiMe$_3$)(dmpe)$_2$Cl]

Calculations were carried out by using the SHELX-76 program package. (See, SHELX-76, a package of crystallographic programs written by G. M. Sheldrick.) All computations were made on a DEC VAX 11/780 computer.

An internal consistency index, R$_{av}$, (See, Silverman et al., *Inorg. Chem.*, 19, 3379 (1980)) was computed to be 2.1% based on 788 symmetry related, low-angle (2$\phi$<30°) reflections (h, $-$k, ±1). The heavy atom position derived from a Patterson map was confirmed through direct methods in centrosymmetric space group I2/a.

Remaining non-hydrogen atoms were located from successive cycles of least-squares refinement, followed by difference Fourier syntheses. Both the niobium and chlorine atoms sit on a two-fold symmetry axis passing through the molecule. Eleven hydrogen atoms were recovered from difference Fourier maps and the rest were fixed, based on the standard geometry [d(C—H)=0.95 Å]. All were constrained to "ride" on carbon atoms to which they were attached. These hydrogen atoms were refined with two common isotropic thermal parameters, one for the methylene (U=0.27 Å$^2$) and one for the methyl groups (U=0.22 Å$^2$), respectively.

Scattering factors used in this and other structural studies reported herein were for neutral atoms and, together with anomalous dispersion corrections for the non-hydrogen atoms, were taken from "International Tables for X-ray Crystallography"; Kynoch Press: Birmingham, England, Vol. IV, pp. 99, 149 (1974). Hydrogen atom scattering factors were as given in Stewart et al., *J. Chem. Phys.*, 42, 3175 (1965)). In the final stages of least-squares refinement, all non-hydrogen atoms were refined anisotropically. Final R factors are reported in Table I; the maximum shift/esd was 0.07.

A final difference electron density map showed no significant electron density. One carbon atom, labelled C3, of the trimethylsilyl group showed large anisotropic thermal parameters, possibly due to some unresolved disorder Final non-hydrogen atomic positional parameters are given in Table II.

EXAMPLE 11

STRUCTURE DETERMINATION AND REFINEMENT COMPOUND (2)
[Ta(Me$_3$SiOCCOSiMe$_3$)(dmpe)$_2$Cl]

The internal consistency index, R$_{av}$=2.0%, computed for 537 symmetry related reflections (h, $-$k, ±1) in the range of 3°<2$\phi$<16° reflects the high quality of the data.

The structure determination and refinement were analogous to that reported for the isostructural molecule, Compound (1). Hydrogen atoms were constrained to "ride" on the carbon atoms to which they were attached.

As with Compound (1), hydrogen atoms were refined with two common isotropic thermal parameters, one for each for the methylene (U=0.33 Å$^2$) and methyl (U=0.20 Å$^2$) groups, respectively. R factors are given in Table I, and the maximum final shift/esd was 0.03.

The final difference electron density map was featureless. Again, there was one carbon atom of the silyl group (C$_3$) that refined with large anisotropic thermal parameters, but a set of disordered positions could not be resolved. Final non-hydrogen atomic positional parameters are given in Table II.

EXAMPLE 12

STRUCTURE DETERMINATION AND REFINEMENT COMPOUND (3)
[Ta(Me$_3$SiOCCOSiMe$_3$)(dmpe)$_2$C$_{10.8}$I$_{0.2}$]

The computed R$_{av}$ based on 87 symmetry-equivalent (0, k, $-$1) reflections was 1.9%. The structure determination and refinement procedures were analogous to those described above for the isostructural molecules, Compounds (1) and (2).

Toward the end of the refinement, and after the structure of Compounds (1) and (2) were known, the rather long Ta-Cl distance (2.727 Å) (see, Bianconi et al., *J. Am. Chem. Soc.*, 108, 311 (1986)) and a 2.6 e$^-$/Å$^3$ electron density peak found in the difference Fourier map near the chloride ion suggested that the crystal might be a mixed halide derivative. Data had been collected on crystals grown from a reaction in which 0.24 mmol of I$_2$ per mmol of Compound (6) was used to activate the magnesium. It therefore seemed likely that there was a contamination of iodide in the compound, since replacement of Cl$^-$ with I$^-$ would not change the molecular geometry.

Removal of the chlorine atom from the model and examination of a difference Fourier map revealed two peaks on the two-fold symmetry axis just barely resolvable, about 0.39 Å apart.

A model was thus introduced in which [Ta(Me₃Si-OCCOSiMe₃)(dmpe)₂Y] molecules, Y=Cl$_x$ and I$_{(1-x)}$, were randomly distributed at the same sites throughout the crystal lattice. Refinement of the site occupancy factor proceeded smoothly to x=0.8. The resulting Ta-Y bond lengths were in good agreement with the expected values. Moreover, the 4:1 Cl to I ratio is the same as the ratio of I₂ to [Ta(CO)₂(dmpe)₂Cl], Compound (6) used in the coupling reaction. The final R-factors thus obtained, (R₁=2.62%, R₂=2.73%, see Table I) are substantially better than those (R₁=4.6%, R₂=4.4%) found for the original model.

Hydrogen atoms were fixed as described for Compound (2), and the common isotropic thermal parameters (U) for both methylene and methyl groups refined to 0.42 and 0.24 Å², respectively. The maximum final shift/esd was 0.026.

A difference Fourier map computed after the fractional iodide contribution was introduced to the model was featureless. The C₃ silyl group carbon atom of this structure also exhibited large anisotropic thermal parameters, as was the case for Compounds (1) and (2). Final non-hydrogen atomic positional parameters are given in Table II.

EXAMPLE 13

STRUCTURE DETERMINATION AND REFINEMENT COMPOUND (3) [Ta(Me₃SiOCCOSiMe₃)(dmpe)₂(OSO₂CF₃)]

The R$_{av}$ value was 3.9% for 805 symmetry related reflections (±h, ±k, ±l) collected in the range 4°<2-φ<36°. The heavy atom was located from a Patterson map and the rest of the non-hydrogen atoms from difference Fourier maps and least-squares refinement cycles.

Difference Fourier maps also yielded 39 hydrogen atoms and the rest were calculated from the expected geometry and constrained to "ride" on carbon atoms to which they were attached. Common isotropic temperature factors (U) refined to 0.09 and 0.14 Å², respectively, for methylene and methyl hydrogen atoms.

EXAMPLE 14

FORMATION OF COMPOUND (7) FROM COMPOUND (2) [TaH(HOCCOH)(dmpe)₂Cl]Cl

The reaction of [Ta(Me₃SiOCCOSiMe₃)(dmpe)₂Cl] compound (2), with 7.6% aqueous HCl affords [TaH(HOCCOH)(dmpe)₂Cl]Cl (7) as a white, crystalline solid in 94% yield. Compound (7) crystallizes in the orthorhombic system, space group P2₁2₁2₁, with a=8.777(2), b=14.856(2), c=18.154(5) Å, and Z=4. The structure consists of a pentagonal-bipyramid with the four atoms of two dmpe ligands and the hydride atom defining the pentagonal plane, and axial positions occupies by the chloride ligand and the midpoint of the HO—C≡C—OH triple bond. Cation (8) is the first known molecule containing the dihydroxyacetylene ligand, characterized by the following structural parameters: Ta—C, 2.058(7) and 2.084(7) Å; C≡C, 1.28(1); C—O, 1.61(9) and 1.367(9) Å; O—C—C, 134.4(7)° and 138.4(7)°. Formation of Compound (7) from Compound (2) occurs formally in two steps, hydrolysis to form the dihydroxyacetylene ligand and oxidative addition of H+ to the tantalum center to form a tantalum hydride bond.

[Ta(Me₃SiOCCOSiMe₃)(dmpe)₂Cl] + H₂O ⟶     eq. (4)
(2)
         [Ta(HOCCOH)(dmpe)₂Cl] + (Me₃Si)₂O

[Ta(HOCCOH)(dmpe)₂Cl] + HCl ⟶     eq. (5)
         [TaH(HOCCOH)(dmpe)₂Cl]Cl
         (7)

Anal. Calcd for C₁₄H₃₅Cl₂O₂P₄Ta (7): C, 27.51; H, 4.77; Cl, 11.60; Found: C, 27.01; H, 5.50; Cl, 12.13. Spectroscopic Data: FAB Mass Spec. M/z=575.1 (M+); FTIR (KBr) 1604 (ν$_{CO}$) cm⁻¹, ¹H NMR (300 MHz, CDCl₃) delta 10.97 (s, OH), 5.06 (t of t, ²J$_{HPtrans}$=90 Hz, ²J$_{HPcis}$=5 Hz), 2.60-1.82 (br M, PCH₂), 1.76 (d, PCH₃, ²J$_{PH}$=9Hz), (d, PCH₃, ²J$_{PH}$=9Hz), 1.48 (d, PCH₃, ²J$_{PH}$=8 Hz), 1.35 (d, PCH₃, ²J$_{PH}$=8 Hz) ppm; ³¹P[¹H] NMR (121 MHz, CDCl₃, referenced to external 85% H₃PO₄) delta 35.55, 14.55 ppm; ¹³C[¹H] NMR (75 MHz, CDCl₃) delta 204.6 ppm.

Crystal data for Compound (7): C₁₄H₃₅Cl₂O₂P₄Ta, M₄=611.18, orthorhombic, Space group P2₁2₁2₁, a=8.777(2), b=14.856(2), c=18.154(5), Z=4, ρ$_{calc}$=1.71 g/cm³. The structure was solved and refined by conventional Patterson, difference Fourier, and full-matrix least-squares techniques. For 2793 unique, observed [I>3 (I)] reflections measured by diffractometer and 212 variable parameters the discrepancy indices were R=2.0%, R$_w$=3.0%.

Selected bond distances (Å) and angles (deg) for Compound (7) are as follows: Ta-Cl, 2.063(7); Ta-C2, 2.084(7); Ta-H3, 1.89(14); Ta-Cl1, 2.526(2); Ta-P1, 2.556(2); Ta-P2, 2.551(2); Ta-P3, 2.618(2); Ta-P4, 2.643(2); C1-O1, 1.35(1); C2-O2, 1.369(9); C1-C2, 1.28(1); O1-H1, 0.99; O2-H2, 1.05; C11-Ta-H3, 96.90; P1-Ta-P2, 120.47(7); P3-Ta-P4, 86.14(7); P1-Ta-P4, 75.04(8); P2-Ta-P3, 75.34(7); Ta-C1-O1, 152.3(5); Ta-C2-O2, 151.1(6); O1-C1-C2, 134.8(7); O2-C2-C1, 137.7(8); C1-O1-H1, 111.07; C2-O2-H2, 105.98.

TABLE I

Experimental Details[a,b] of the X-ray Diffraction Studies of [Nb(Me₃SiOCCOSiMe₃)(dmpe)₂Cl] (1), [Ta(Me₃SiOCCOSiMe₃)(dmpe)₂Cl] (2), [Ta(Me₃SiOCCOSiMe₃)(dmpe)₂Cl₀.₈I₀.₂] (3), and [Ta(Me₃SiOCCOSiMe₃)(dmpe)₂(OSO₂CF₃)](4).

| | 1 | 2 | 3 | 4 |
|---|---|---|---|---|
| formula | C₂₀H₅₀ClO₂P₄Si₂Nb | C₂₀H₅₀ClO₂P₄Si₂Ta | C₂₀H₅₀Cl₀.₈I₀.₂O₂P₄SSi₂Ta | C₂₁H₅₀F₃O₅P₄Si₂Ta |
| a, Å | 16.485 (2) | 16.432 (3) | 16.399 (2) | 16.381 (3) |
| b, Å | 10.857 (2) | 10.864 (3) | 10.945 (3) | 12.389 (2) |
| c, Å | 19.274 (2) | 19.224 (8) | 19.209 (5) | 18.626 (2) |
| β, deg | 106.43 (1) | 106.40 (2) | 106.51 (1) | 103.60 (2) |
| V, Å³ | 3309 | 3292 | 3306 | 3674 |
| formula weight | 631.05 | 719.09 | 737.38 | 832.7 |
| Z | 4 | 4 | 4 | 4 |
| σ$_{calcd}$[f] | 1.267 | 1.451 | 1.481 | 1.505 |
| Space Group | I2/a | I2/a | I2/a | P2₁/c |
| radiation[d] | | Mo K$_α$ (0.71069) Å | | Cu K$_α$ (1.5418 Å) |
| data limits, deg | 3 < 2θ < 54 | 3 < 2θ < 57 | 3 < 2θ < 45 | 4 < 2θ < 112 |

TABLE I-continued

Experimental Details[a,b] of the X-ray Diffraction Studies of [Nb(Me₃SiOCCOSiMe₃)(dmpe)₂Cl] (1), [Ta(Me₃SiOCCOSiMe₃)(dmpe)₂Cl] (2), [Ta(Me₃SiOCCOSiMe₃)(dmpe)₂Cl₀.₈I₀.₂] (3), and [Ta(Me₃SiOCCOSiMe₃)(dmpe)₂(OSO₂CF₃)](4).

|  | 1 | 2 | 3 | 4 |
|---|---|---|---|---|
| crystal dimensions, mm | 0.375 × 0.3 × 0.2 | 0.375 × 0.25 × 0.125 | 0.20 × 0.32 × 0.54 | 0.4 × 0.325 × 0.25 |
| linear abs. coeff., cm⁻¹[e] | 6.48 | 35.25 | 35.04 | 82.57 |
| no. of data collected | 3617 | 4158 | 3244 | 4776 |
| no. of unique data[f] | 2437 | 2933 | 2350 | 3024 |
| no. of parameters refined | 139 | 139 | 144 | 336 |
| R₁[g] | 0.0361 | 0.0370 | 0.0262 | 0.0472 |
| R₂[h] | 0.0410 | 0.0393 | 0.0273 | 0.0473 |

[a] Data were collected by $\theta/2\theta$ scans on an Enraf-Nonius CAD-4F κ-geometry diffractometer at 23 ± 1° C.
[b] Calculations were performed on a DEC VAX 11/780 computer using SHELX-76.
[c] Since the crystals decompose, their densities could not be measured.
[d] In case of Cu radiation, no monochromator was used.
[e] Absorption corrections were performed either empirically from psi scans or with the Wehe-Busing-Levy ORABS programs.
[f] $I > 3\sigma (I)$ was used.
[g] $R_1 = \Sigma||F_o| - |F_c||/\Sigma|F_o|$.
[h] $R_2 = \{\Sigma w||F_o| - |F_c||^2/\Sigma w|F_o|^2\}$.

TABLE II

Non-hydrogen Atomic Coordinates for Compounds 1, 2, and 3.[a]

| | Compound 1, M = Nb | | | Compound 2, M = Ta | | | Compound 3, M = Ta[b] | | |
|---|---|---|---|---|---|---|---|---|---|
| atom | x | y | z | x | y | z | x | y | z |
| M | 0.2500 | 0.21771 (4) | 0.0000 | 0.2500 | 0.21713 (3) | 0.0000 | 0.2500 | 0.21798 (2) | 0.0000 |
| Cl | 0.2500 | 0.45495 (12) | 0.0000 | 0.2500 | 0.4539 (2) | 0.0000 | 0.2500 | 0.4531 (8) | 0.0000 |
| P1 | 0.37600 (7) | 0.26601 (10) | 0.11049 (6) | 0.37554 (12) | 0.26788 (17) | 0.10983 (9) | 0.37625 (10) | 0.26776 (13) | 0.10980 (8) |
| P2 | 0.37285 (8) | 0.25066 (10) | −0.05562 (4) | 0.37182 (13) | 0.24985 (18) | −0.05584 (11) | 0.37193 (10) | 0.25028 (14) | −0.05576 (9) |
| Si | 0.29689 (8) | −0.15437 (10) | 0.12607 (6) | 0.29811 (12) | −0.15443 (18) | 0.12616 (9) | 0.29797 (10) | −0.15115 (14) | 0.12634 (7) |
| O | 0.32768 (15) | −0.0565 (2) | 0.07334 (13) | 0.3279 (2) | −0.0571 (4) | 0.0725 (2) | 0.3280 (2) | −0.0551 (3) | 0.07328 (18) |
| C | 0.2799 (2) | 0.0365 (3) | 0.03076 (17) | 0.2815 (3) | 0.0372 (5) | 0.0310 (3) | 0.2811 (3) | 0.0392 (4) | 0.0305 (2) |
| C1 | 0.1962 (3) | −0.2283 (4) | 0.0802 (3) | 0.1969 (5) | −0.2319 (7) | 0.0808 (5) | 0.1951 (4) | −0.2256 (6) | 0.0808 (4) |
| C2 | 0.3836 (4) | −0.2676 (5) | 0.1505 (4) | 0.3851 (6) | −0.2690 (9) | 0.1484 (6) | 0.3832 (5) | −0.2659 (8) | 0.1483 (5) |
| C3 | 0.2862 (5) | −0.0765 (7) | 0.2077 (3) | 0.2901 (8) | −0.0763 (12) | 0.2098 (5) | 0.2917 (7) | −0.0743 (11) | 0.2115 (4) |
| C11 | 0.3671 (5) | 0.3777 (7) | 0.1794 (3) | 0.3694 (6) | 0.3755 (12) | 0.1795 (5) | 0.3717 (6) | 0.3742 (9) | 0.1818 (4) |
| C12 | 0.4375 (4) | 0.1458 (6) | 0.1662 (4) | 0.4369 (6) | 0.1447 (10) | 0.1656 (6) | 0.4385 (6) | 0.1434 (9) | 0.1632 (6) |
| C13 | 0.4581 (5) | 0.3390 (9) | 0.0786 (4) | 0.4563 (7) | 0.3489 (16) | 0.0796 (6) | 0.4586 (6) | 0.3479 (14) | 0.0787 (5) |
| C23 | 0.4667 (4) | 0.3085 (8) | 0.0118 (4) | 0.4677 (6) | 0.3082 (12) | 0.0125 (6) | 0.4684 (5) | 0.3070 (10) | 0.0116 (5) |
| C21 | 0.3679 (4) | 0.3613 (6) | −0.1272 (3) | 0.3652 (6) | 0.3551 (11) | −0.1304 (5) | 0.3661 (6) | 0.3478 (10) | −0.1312 (5) |
| C22 | 0.4148 (4) | 0.1150 (5) | −0.0877 (4) | 0.4130 (6) | 0.1138 (9) | −0.0886 (6) | 0.4127 (6) | 0.1191 (8) | −0.0880 (6) |
| I | — | — | — | — | — | — | 0.2500 | 0.4826 (8) | 0.0000 |

[a] Numbers in parentheses are errors in the last significant digit(s). See FIG. 1 for atom-labeling scheme.
[b] Site occupancy factors are 0.8 for Cl and 0.2 for I.

The present invention has been described in detail, including the preferred embodiments thereof. However, it will be appreciated that those skilled in the art, upon consideration of the present disclosure, may make modifications and/or improvements on this invention and still be within the scope and spirit of this invention as set forth in the following claims.

What is claimed is:

1. A process for the formation of an isolable compound containing a C—X—C, C—X—N, or N—X—N group, where X is selected from the group consisting of a single, double, or triple bond consisting of the steps:

(a) reacting an early transition metal seven coordinate complex of the formula (I) with a reducing agent and a Lewis Acid;

(I)

wherein;

M is an early transition metal selected from the group consisting of titanium, zirconium, molybdenum, tungsten, manganese, technetium, and rhenium;

Y₁ and Y₂ are each linear carbon containing ligands independently selected from the group consisting of C≡O, CNR, NCR, C≡CR, CN, C=S, CO₂ and CS₂, wherein R is hydrogen, an alkyl group, or an aryl group;

L₁, L₂, L₃, and L₄, are each neutral 2-electron donor ligands;

X is halogen or pseudohalogen; and (b) reacting the species formed in step (a) with a sufficient quantity of a second Lewis Acid such that the isolable species containing a C—X—C, C—X—N, or N—X—N group, where X is selected from the group consisting of a single, double, or triple bond is formed.

2. The process of claim 1, wherein the second Lewis Acid is selected from the group consisting of compounds having the formula R₃SiX, wherein R is a C₁ to C₆ alkyl and X is selected from the group consisting of halogen, H⁺ and aluminum halides and mixtures thereof.

3. The process of claim 1, wherein the reducing agent is activated magnesium.

4. The process of claim 3, wherein the magnesium is activated with I₂.

5. The process of claim 3, wherein the magnesium is activated with HgCl₂.

6. The process of claim 2, wherein the reducing agent is Mg-anthracene.

7. The process of claim 1, 2, 3, 4, or 5, wherein the Lewis Acids are one or more compounds or ions containing elements selected from the group consisting of the elements of Group I, II, III, and IV of the Period Table of the Elements.

8. The process of claim 1, wherein the reducing agent is sodium amalgam.

9. The process of claim 8, wherein the amalgam is from 30% to 50% sodium in mercury.

10. The process of claim 8, wherein the amalgam is about 40% sodium in mercury.

11. The compound having the formula:

[Nb(Me$_3$SiOCCOSiMe$_3$)(1,2-bis(dimethylphosphino)ethane)$_2$Cl]

prepared by the process of claim 1.

12. The compound having the formula:

[Ta(Me$_3$SiOCCOSiMe$_3$)(1,2-bis(dimethylphosphino)ethane)$_2$Cl]

prepared by the process of claim 1.

13. The compound having the formula:

[Ta(Me$_3$SiOCCOSiMe$_3$)(1,2-bis(dimethylphosphino)ethane)$_2$C$_{10.8}$I$_{0.2}$]

prepared by the process of claim 1.

14. The compound having the formula:

[Ta(Me$_3$SiOCCOSiMe$_3$)(1,2-bis(dimetnylphosphino)ethane)$_2$(OTf)]

prepared by the process of claim 1.

15. The process of forming a compound having the formula (II):

wherein:
M is an early transition metal selected from the group consisting of titanium, zirconium, hafnium, vanadium, niobium, tantalum, chromium, molybdenum, tungsten, manganese, technetium, and rhenium;

L$_{1-4}$ are each independently selected from ligands that are neutral 2-electron donors; and X$_1$ and X$_2$ are each independently halogen or pseudohalogen; which comprises a two step reaction, the first step of which involves the hydrolysis and the second step of which involves the oxidation of the compound having the formula (III)

with protons from a suitable source.

16. The process of claim 15, wherein aqueous hydrochloric acid is used to provide the necessary protons.

17. The process of claim 15, wherein water is used to provide the necessary protons.

18. The process of claim 15, wherein methanol is used to provide the necessary protons.

19. The compound having the formula:

[TaH(HOCCOH)(1,2-bis(dimethylphosphino)ethane)$_2$Cl]Cl prepared by the process of claim 16.

* * * * *